US008022254B2

(12) United States Patent
Redlingshöfer et al.

(10) Patent No.: US 8,022,254 B2
(45) Date of Patent: Sep. 20, 2011

(54) CATALYSTS COMPRISING HALIDE-CONTAINING ALKALI TUNGSTATES FOR THE SYNTHESIS OF ALKYLMERCAPTAN, AND PROCESS FOR THEIR PREPARATION

(75) Inventors: Hubert Redlingshöfer, Münchesteinach (DE); Christoph Weckbecker, Gründau-Lieblos (DE); Andreas Dörflein, Grosskrotzenburg (DE)

(73) Assignee: Evonik Degussa GmbH, Essen (DE)

( * ) Notice: Subject to any disclaimer, the term of this patent is extended or adjusted under 35 U.S.C. 154(b) by 794 days.

(21) Appl. No.: 11/304,438

(22) Filed: Dec. 15, 2005

(65) Prior Publication Data
US 2006/0135816 A1 Jun. 22, 2006

(30) Foreign Application Priority Data

Dec. 18, 2004 (DE) .................. 10 2004 061 016

(51) Int. Cl.
*C07C 319/08* (2006.01)
*B01J 21/14* (2006.01)
*B01J 21/08* (2006.01)
(52) U.S. Cl. .......... 568/71; 502/254; 502/304; 502/317; 502/305; 423/263; 423/594.13
(58) Field of Classification Search ............ 568/71; 502/254
See application file for complete search history.

(56) References Cited

U.S. PATENT DOCUMENTS

| 2,820,062 | A | | 1/1958 | Folkins et al. |
| 3,373,097 | A | * | 3/1968 | Gomes et al. ............. 205/371 |
| 5,852,219 | A | * | 12/1998 | Sauer et al. .................. 568/71 |
| 7,592,288 | B2 | * | 9/2009 | Redlingshofer et al. ...... 502/317 |
| 7,687,667 | B2 | * | 3/2010 | Brand et al. .................. 568/71 |
| 7,759,523 | B2 | * | 7/2010 | Redlingshofer et al. ....... 568/71 |
| 2005/0080295 | A1 | | 4/2005 | Redlingshofer et al. |

FOREIGN PATENT DOCUMENTS

| EP | 0 068 193 A1 | 1/1983 |
| EP | 0 832 687 A2 | 4/1998 |
| EP | 0 832 878 A2 | 4/1998 |
| WO | WO 2004/096760 A1 | 11/2004 |
| WO | WO 2005/021491 A1 | 3/2005 |
| WO | WO 2006/015668 A1 | 2/2006 |

OTHER PUBLICATIONS

Mashina, A.V. et al., "Activity of Tungstate Catalysts in the Synthesis of Methylmercaptane from Methanol and Hydrogen Sulfide." Reaction Kinetics Catalysis Letters, 1988, pp. 159-164, vol. 36, No. 1, Elsevier, Amsterdam, Netherlands.

* cited by examiner

*Primary Examiner* — Melvin Mayes
*Assistant Examiner* — Yun Qian
(74) *Attorney, Agent, or Firm* — Smith, Gambrell & Russell, LLP

(57) ABSTRACT

The invention relates to a halide-containing alkali tungstate catalyst for the synthesis of alkylmercaptans from alkanols and hydrogen sulfide, and to a process for the preparation of this catalyst.

30 Claims, No Drawings

CATALYSTS COMPRISING HALIDE-CONTAINING ALKALI TUNGSTATES FOR THE SYNTHESIS OF ALKYLMERCAPTAN, AND PROCESS FOR THEIR PREPARATION

REFERENCE TO RELATED APPLICATIONS

This application claims the benefit of German priority application 10 2004 061 016.9 filed Dec. 18, 2004.

INTRODUCTION AND BACKGROUND

The present invention relates to a catalyst comprising halide-containing alkali tungstates for the synthesis of alkylmercaptans from alkanols and hydrogen sulfide, and to a process for the preparation of this catalyst.

The term "alkali" is to be understood as meaning bonded alkali metals according to the periodic system of the elements, it also being possible for the tungstates to contain two or more different bonded alkali metals. The term "halide" is to be understood as meaning the bonded halogens of the periodic system of the elements, it also being possible for the alkali tungstates according to the invention to contain two or more different halides.

Among the alkylmercaptans, methylmercaptan in particular is an industrially important intermediate, for example for the synthesis of methionine and also for the synthesis of dimethyl sulfoxide and dimethylsulfone. Nowadays, it is prepared predominantly from methanol and hydrogen sulfide by reaction on a catalyst of aluminum oxide. The synthesis of methylmercaptan is usually carried out in the gas phase at temperatures of from 300 to 500° C. and at pressures of from 1 to 25 bar.

As well as containing the methylmercaptan that is formed, the reaction mixture contains unreacted starting materials and secondary products, such as, for example, dimethyl sulfide and dimethyl ether, as well as gases that are inert in terms of the reaction, such as, for example, methane, carbon monoxide, hydrogen and nitrogen. The methylmercaptan that forms is separated off from this reaction mixture.

For the economy of the process, it is necessary for the yield in the catalytic reaction of methanol and hydrogen sulfide to methylmercaptan to be as high as possible, in order to keep the outlay in terms of the separation of the resulting methylmercaptan from the reaction mixture as low as possible. In particular, the energy outlay for cooling the reaction gas mixture in order to condense the methylmercaptan represents a major cost factor here.

In order to increase the activity and selectivity, potassium tungstate or caesium tungstate is usually added to aluminum oxide as support. The tungstate is usually used in amounts of up to 25 wt. %, based on the total weight of the catalyst. An improvement in the activity and selectivity is also obtained by increasing the molar ratio of hydrogen sulfide to methanol. Molar ratios of from 1 to 10 are conventionally used.

However, a high molar ratio also means a high excess of hydrogen sulfide in the reaction mixture and hence the necessity of circulating large amounts of gas. In order to reduce the energy outlay required therefore, the ratio of hydrogen sulfide to methanol should therefore differ only slightly from 1.

U.S. Pat. No. 2,820,062 relates to a process for the preparation of organic thiols, in which there is used a catalyst of active aluminum oxide to which potassium tungstate has been added in an amount of from 1.5 to 15 wt. %, based on the weight of the catalyst. With this catalyst, good activities and selectivities are achieved at reaction temperatures of 400° C. and molar ratios of 2. This U.S. patent specification mentions various possibilities for incorporating the potassium tungstate into the aluminum oxide. For example, impregnation processes, coprecipitations and pure mixtures are said to be usable. The actual preparation of the catalyst is accorded little importance for the economy of the synthesis process of methylmercaptan. EP 0 832 687 B1 describes the advantages of the use of caesium tungstate ($Cs_2WO_4$) as promoter instead of potassium tungstate ($K_2WO_4$). For example, increased activity with simultaneous good selectivity can be achieved by the use of caesium tungstate.

By increasing the caesium tungstate concentration to up to 40 wt. %, the selectivity in respect of methylmercaptan can be increased to up to 92% without the activity being disproportionately impaired.

The general opinion is that the best selectivity is achieved with catalysts in which the alkali/tungstate ratio is 2:1 (A. V. Mashkina et al., React. Kinet. Catal. Lett., Vol. 36, No. 1, 159-164 (1988)).

The object of the present invention is to provide a catalyst and a process for its preparation, which catalyst is distinguished at low molar ratios of hydrogen sulfide to methanol by improved activity and selectivity compared with the known catalysts and accordingly results in a better yield and greater economy of the process.

SUMMARY OF THE INVENTION

This object is achieved by the provision of a catalyst comprising a catalytically active alkali tungstate which contains in particular bonded alkali metals and tungsten in a molar ratio of alkali metals to tungsten of <4:1, in particular from 3:1 to 0.9:1, preferably from 2.4:1 to 1:1, especially from 2.2:1 to 1.2:1, and also halide(s), in particular halides and alkali metals in a molar ratio of from 0.01:1 to 3:1, preferably from 0.01:1 to 1:1, especially from 0.1:1 to 1:1.

The catalytically active halide-containing compound according to the invention generally has the formula

$$A_xWO_yX_z, \quad (I)$$

wherein A: represents at least one alkali metal, in particular selected from the group Na, K, Cs, Rb;

X: represents least one halide selected from the group F, Cl, Br, I, x: is from 0.9 to <4, in particular from 1.2 to 3;

y: this value is established according to the structure of the tungstate and the alkali content on the basis of the hexavalence of the tungsten;

z: is from 0.01 to <12, in particular from 0.9 to <4.

The size of z is a measure of the halide content in the tungstate, which does not have to be bonded chemically to the tungstate.

The halide constituent of the composition according to formula (I) consists of or comprises chloride in particular when the tungstate contains at least two different bonded alkali metals and/or at least one further halide selected from the group F, Br, I.

Chloride is preferably present as the only halide when the molar ratio of Na or K/W in the catalyst is from >0.9 to 1.9.

The alkali constituent of the catalytically active compound can be composed of one or more elements of the alkali group. Likewise, the bonded halogen constituent of the catalyst may be composed of one or more different halides.

If the catalyst is in the form of a supported catalyst, it comprises the halide-containing alkali tungstate in an amount of from 8 to 50 wt. %, in particular from 15 to 40 wt. %, preferably from 20 to 36 wt. %. In the case of a shell catalyst, these amounts relate to the composition of the shell.

The halogen-containing oxidic compounds of alkali metal (s) and tungsten can be impregnated directly onto a support body (supported catalyst).

DETAILED DESCRIPTION OF INVENTION

When preparing catalysts in the form of extrudates or pressed bodies, the pulverulent support is impregnated or mixed with the oxidic composition according to the invention, and the resulting intermediate is then shaped (full catalyst). If a shell catalyst is prepared, the pulverulent support is impregnated with the catalytically active composition and the resulting mixture is then applied in the form of a shell to a support core, preferably an inert support core.

The molar halide/alkali ratio is particularly preferably from 0.1:1 to 1:1. Unlike the catalysts according to the prior art impregnated with caesium tungstate ($Cs_2WO_4$) or potassium tungstate ($K_2WO_4$), the tungstates according to the invention for the reaction of alkanols with hydrogen sulfide to form alkylmercaptans contain an amount of halides.

It has been found that the content of halides, in particular in the aluminum oxide that is preferably used, in comparison with the halide-free alkali tungstate solely used in the prior art, imparts to the catalyst a markedly improved activity, while at the same time the selectivity is high. Furthermore, as a result of the addition of halides to the alkali tungstate, excellent selectivity is unexpectedly observed, with very high degrees of conversion of alcohol. According to the invention it is possible, with very high loading with the promoter, to achieve an excellent conversion without the selectivity of the catalyst falling, as is known from the prior art for halide-free catalysts. Furthermore, it has been found that the activity and selectivity of the catalyst can be adjusted in a targeted manner via the alkali tungsten-halide ratio and via the choice of alkali metals and halides. As a result of the possibility of using mixtures of compounds of different alkali metals or halogens, comparatively expensive substances such as caesium, rubidium, bromine or iodine compounds can be at least partially replaced by less expensive substances, such as, for example, potassium or sodium compounds or chlorides, without any impairment of the activity or selectivity of the catalyst.

The catalyst is preferably used in the form of a supported catalyst, in which the surface is impregnated with the catalytically active substance, or in the form of a shell catalyst, in which a core, preferably an inert core, is surrounded by a mixture of catalytically active substance and support material. Furthermore, it is also possible to use extrudates or pressed bodies, in which the catalytically active substance is mixed with the pulverulent support material before shaping or which are impregnated therewith.

There are used as support materials the known oxidic inorganic compounds, such as, for example, $SiO_2$, $TiO_2$, $ZrO_2$ and, preferably, so-called active aluminum oxide. This material has high specific surface areas of approximately from 10 to 400 $m^2/g$ and consists predominantly of oxides of the transition group of the crystallographic phases of aluminum oxide (see, for example, Ullmann's Encyclopedia of Industrial Chemistry of 1985, Vol. A1, pages 561-562). These transition oxides include γ-, δ-, η-, κ-, χ- and θ-aluminum oxide. All these crystallographic phases are converted into thermally stable α-aluminum oxide when the aluminum oxide is heated to temperatures above 1100° C. Active aluminum oxide is supplied commercially for catalytic applications in various qualities and delivery forms. Particularly suitable for the preparation of supported catalysts are moulded bodies of granulated or extruded aluminum oxide having grain diameters of from 1 to 5 mm, a specific surface area of from 180 to 400 $m^2/g$, a total pore volume of from 0.3 to 1.2 ml/g and a bulk density of from 300 to 900 g/l. For the purposes of the invention, preference is given to the use of aluminum oxide having a specific surface area greater than 200 $m^2/g$, because the catalytic activity of the finished catalyst increases slightly as the surface area of the aluminum oxide increases. This material is used in powder form preferably for the preparation of the shell catalysts, extrudates or pressed bodies.

According to the invention, the support material is not generally pretreated with hydrohalic acid.

The aqueous impregnation solution for applying the promoter can be prepared in a simple manner from water-soluble alkali, tungsten and halogen compounds, in particular tungstic acid ($H_2WO_4$), alkali hydroxides, alkali halides and optionally ammonium halides or hydrohalic acid. To this end, for example, tungstic acid is suspended in water and dissolved with the addition of a base and with heating. The desired alkali halide(s) or ammonium halides, optionally also the corresponding hydroxides and/or, for example, a hydrohalic acid with the desired halide, are likewise dissolved in water and combined with the solution of tungstic acid (promoter solution) in such a manner that the desired composition ratios for the alkali tungstates and their halide content are obtained. In addition to the alkali halides there may advantageously be used also alkali salts whose anions can be expelled by heat treatment without leaving a residue, such as, for example, nitrates, formates, oxalates, acetates or carbonates. In order to stabilise the promoter solution with a pH of preferably from 8 to 14, inorganic and also organic bases are used. Preference is given to the use of those which can be expelled by subsequent heat treatment of the catalyst obtained after the impregnation, without leaving a residue. Such bases preferably include ammonium hydroxide and organic bases, in particular amines.

As a result of this procedure, the acidic groups present on the surface of, for example, $Al_2O_3$ support materials are largely neutralised, generally to the extent of at least about 75%, in particular 100%.

The molar ratio of alkali metal compounds and halides in the aqueous impregnation solution is so chosen that the novel tungstates contain halides and alkali metals in a molar ratio of from 0.01:1 to 3:1. In comparison with the known halide-free catalysts, this results in a markedly increased yield when the catalysts according to the invention are used, in particular with low ratios of hydrogen sulfide and methanol in the reaction gas.

Preference is given to caesium, potassium and rubidium tungstates, in particular caesium tungstates; preferred halides are fluoride, bromide and chloride, in particular fluoride and bromide.

Tungstates having different alkali cations or contents of different halides preferably contain cations of two different alkali metals and at least one halide in a ratio of alkali to halide of from 0.01:1.0 to 3.0:1.0, the molar contents of alkali metals or different halides that are optionally present being counted as the sum. As a countermove, the content of the less expensive alkali metal or halide is increased to such an extent, and at the same time the content of the comparatively more expensive alkali metal or halide is lowered, so that the activity or selectivity of the catalyst is not impaired.

In the case of combinations of alkali metals, preference is given to tungstates in which the Cs or Rb content is replaced, in an advantageous ratio, by K or Na cations.

Preference is given to catalysts in which combinations of bonded alkali metals from the group:
a) potassium and caesium,
b) sodium and caesium,
c) rubidium and caesium,
d) sodium and potassium,
e) rubidium and potassium exist that vary from a molar ratio of 1:1.

Various impregnation techniques can be used for applying the promoter solution, such as immersion impregnation, spray impregnation, vacuum impregnation and pore volume impregnation, it also being possible for the impregnation to be carried out repeatedly. In the case of shaped bodies, the chosen impregnation process must allow the desired amount of promoter to be applied with good uniformity over the entire cross-section.

The promoter solution is preferably applied to the shaped bodies by spray or vacuum impregnation in one or two steps. In the case of spray impregnation, the aqueous impregnation solution is sprayed onto the support bodies. In vacuum impregnation, a reduced pressure is produced by means of a vacuum pump in a container filled with shaped bodies. By opening a hose connection to the aqueous impregnation solution, the solution is drawn into the container until the entire bulk of shaped bodies is covered with solution. After an impregnation time of from 0.2 to 2 hours, the solution that has not been taken up by the material is discharged or poured away.

The initial concentration gradient can be largely made equal over the cross-section of the shaped bodies by predrying for a period of from 1 to 10 hours at room temperature. In this manner, the uniformity of the impregnation over the cross-section of the catalyst particles is improved. Preferably, the catalyst precursors so obtained are dried for a period of from 1 to 10 hours at from 100 to 200° C., preferably at from 100 to 400° C., in order to remove residual moisture. Calcination is then carried out for a period of from 1 to 20 hours, preferably from 1 to 5 hours, at from 300 to 600° C., preferably from 420 to 480° C. As a result, the promoter is fixed on the aluminum oxide and the base of the impregnation solution is decomposed and expelled. Optionally, a stream of gas can flow through the bulk of the support bodies of the catalyst precursors during predrying, drying and calcination, the stream of gas improving the removal of the residual moisture and the decomposition gases.

It is also possible for the impregnation of the shaped bodies to be carried out in a plurality of steps, in particular in two steps.

In this preferred embodiment, the solution used in the first step then contains from one to two thirds of the intended total amount of alkali and tungsten compounds.

If the procedure is carried out in a plurality of steps, but at least in two steps, the precursor obtained in the first step is optionally not calcined.

Otherwise, the same impregnation, drying and calcination programme as described for the one-step process is carried out in the second step.

Such multistep impregnation is expedient in particular when high loading is desired and/or the limited solubility of the promoter mixture does not permit loading in one step.

It is also possible to spray the support bodies or support material with the impregnation solution repeatedly during the impregnation operation (step a from claim 22) and, between these treatment steps, to remove portions of the residual moisture at a temperature of up to 120° C., before proceeding to step b.

When preparing the shell catalyst, the powder that is to be applied to form a shell can be calcined before or after the coating. For example, this type of catalyst can be prepared in accordance with EP-B-0 068 193. When preparing the extrudates or pressed bodies, the calcination can also be carried out before and/or after the shaping.

EXAMPLES

Example 1

Comparison Example 150 g of aluminum oxide (Spheralite 501A) were impregnated with 21.0 wt. % caesium tungstate ($Cs_{2.0}WO_4$) by means of vacuum impregnation. To this end, the procedure, in detail, was as follows:

For the preparation of the impregnation solution, 55.7 g of tungstic acid were suspended 44.5 g of water and dissolved by the addition of 111.4 g of 25% ammonia solution and heating to 50° C. 74.6 g of $Cs(OH).H_2O$ were dissolved in 37.3 g of water and mixed with the first solution. The solution was then stirred for 48 hours in a covered glass beaker. The solution was then made up to a volume of 234 ml with 25 g of water.

The aluminum oxide was placed in a glass vessel which had been evacuated to 150 mbar. By opening a tap, the impregnation solution was drawn into the evacuated glass vessel until the entire bulk of shaped bodies was covered with the solution. After a waiting time of 15 minutes and aeration of the glass vessel, the solution that had not been taken up by the aluminum oxide flowed back into the glass beaker. 79 ml of impregnation solution were thereby taken up by the aluminum oxide.

The granules were dried for a period of one hour at room temperature in a stream of air and then at 120° C. for 3 hours in order to remove residual moisture. The granules were then calcined for 3 hours at 455° C.

Example 2

Comparison Example

Example 1 was repeated with 26.3% loading of the aluminum oxide with caesium tungstate ($Cs_{2.0}WO_4$).

Example 3

Comparison Example

Comparison example 1 was repeated with 19.6% loading of the aluminum oxide with potassium tungstate ($K_{2.0}WO_4$) using KOH instead of $Cs(OH).H_2O$.

Example 4

150 g of aluminum oxide (Spheralite 501A) were impregnated with 22.3 wt. % fluoride-containing caesium tungstate by means of vacuum impregnation. To this end, the procedure, in detail, was as follows:

For the preparation of the impregnation solution, 56.8 g of tungstic acid were suspended 45.4 g of water and dissolved by the addition of 113.6 g of 25% ammonia solution and heating to 50° C. 68.8 g of CsF were dissolved in 40.0 g of water and mixed with the first solution. The solution was then stirred for 4 hours in a covered glass beaker. The solution was then made up to a volume of 234 ml with 24.9 g of water.

The aluminum oxide was placed in a glass vessel which had been evacuated to 150 mbar. By opening a tap, the impregnation solution was drawn into the evacuated glass vessel until the entire bulk of shaped bodies was covered with the solution. After a waiting time of 15 minutes and aeration of the glass vessel, the solution that had not been taken up by the aluminum oxide flowed back into the glass beaker. 73 ml of impregnation solution were thereby taken up by the aluminum oxide.

The granules were dried for a period of one hour at room temperature in a stream of air and then at 120° C. for 3 hours in order to remove residual moisture. The granules were then calcined for 3 hours at 455° C.

Example 5

150 g of aluminum oxide (Spheralite 501A) were impregnated in one impregnation with a total of 23.9 wt. % chlorine-containing caesium tungstate by means of vacuum impregnation. To this end, the procedure, in detail, was as follows:

57.8 g of tungstic acid were suspended 46.2 g of water and dissolved by the addition of 115.6 g of 25% ammonia solution and heating to 50° C. 77.6 g of CsCl were dissolved in 30.0 g of water and mixed with the first solution. The solution was then stirred for 22 hours in a covered glass beaker. The solution was then made up to a volume of 234 ml with 23.2 g of water. The aluminum oxide was placed in a glass vessel which had been evacuated to 150 mbar. By opening a tap, the impregnation solution was drawn in until the entire bulk of shaped bodies was covered with the solution. After a waiting time of 15 minutes and aeration of the glass vessel, the solution that had not been taken up by the aluminum oxide flowed back into the glass beaker. 74 ml of impregnation solution were thereby taken up by the aluminum oxide. The granules were then dried for one hour at room temperature and for 3 hours at 120° C. and calcined for 3 hours at 455° C.

Example 6

150 g of aluminum oxide (Spheralite 501A) were impregnated in a two-step impregnation with a total of 18.5 wt. % bromide-containing caesium tungstate by means of vacuum impregnation. To this end, the procedure, in detail, was as follows:

58.5 g of tungstic acid were suspended 46.8 g of water and dissolved by the addition of 116.9 g of 25% ammonia solution and heating to 50° C. 15.6 g of CsBr and 50.4 g of Cs(OH).H$_2$O were dissolved in 30.0 g of water and mixed with the first solution. The solution was then stirred for 21 hours in a covered glass beaker. The solution was then made up to a volume of 234 ml with 17.2 g of water. The aluminum oxide was placed in a glass vessel which had been evacuated to 150 mbar. By opening a tap, the impregnation solution was drawn in until the entire bulk of shaped bodies was covered with the solution. After a waiting time of 15 minutes and aeration of the glass vessel, the solution that had not been taken up by the aluminum oxide flowed back into the glass beaker. 81 ml of impregnation solution were thereby taken up by the aluminum oxide. The granules were then dried for one hour at room temperature and for 3 hours at 120° C. and calcined for 3 hours at 455° C.

Example 7

150 g of aluminum oxide (Spheralite 501A) were impregnated in one impregnation with a total of 29.6 wt. % iodine-containing caesium tungstate by means of vacuum impregnation. To this end, the procedure, in detail, was as follows:

64.1 g of tungstic acid were suspended 51.3 g of water and dissolved by the addition of 128.2 g of 25% ammonia solution and heating to 50° C. 132.7 g of CsI were dissolved in 30.0 g of water and mixed with the first solution. The solution was then stirred for 6 hours in a covered glass beaker. The solution was then made up to a volume of 234 ml with 6 g of water. The aluminum oxide was placed in a glass vessel which had been evacuated to 150 mbar. By opening a tap, the impregnation solution was drawn in until the entire bulk of shaped bodies was covered with the solution. After a waiting time of 15 minutes and aeration of the glass vessel, the solution that had not been taken up by the aluminum oxide flowed back into the glass beaker. 80 ml of impregnation solution were thereby taken up by the aluminum oxide. The granules were then dried for one hour at room temperature and for 3 hours at 120° C. and calcined for 3 hours at 455° C.

Example 8

95 g of aluminum oxide (Spheralite 501A) were impregnated in one impregnation with a total of 23.5 wt. % fluoride- and bromide-containing caesium tungstate by means of vacuum impregnation. To this end, the procedure, in detail, was as follows:

36.8 g of tungstic acid were suspended in 35.0 g of water and dissolved by the addition of 73.6 g of 25% ammonia solution and heating to 50° C. 22.3 g of CsF and 31.2 g of CsBr were dissolved in 30.0 g of water and mixed with the first solution. The solution was then stirred for 22 hours in a covered glass beaker. The solution was then made up to a volume of 234 ml with 1 g of water. The aluminum oxide was placed in a glass vessel which had been evacuated to 150 mbar. By opening a tap, the impregnation solution was drawn in until the entire bulk of shaped bodies was covered with the solution. After a waiting time of 15 minutes and aeration of the glass vessel, the solution that had not been taken up by the aluminum oxide flowed back into the glass beaker. 44 ml of impregnation solution were thereby taken up by the aluminum oxide. The granules were then dried for one hour at room temperature and for 3 hours at 120° C. and calcined for 3 hours at 455° C.

Example 9

Application Example

The catalysts were tested in respect of their performance data in the synthesis of methylmercaptan from hydrogen sulfide and methanol.

The synthesis was carried out in a stainless steel tube having an inside diameter of 18 mm and a length of 500 mm. The bulk catalyst of in each case 76 ml was fixed in the reaction tube by inert fillings of glass spheres on both sides. The reaction tube was heated to the reaction temperature of about 320° C. via a double-walled jacket containing a heating oil.

The test conditions are to be found in the following list:
GHSV: 1300 h$^{-1}$ (based on standard conditions)
LHSV: 0.84 h$^{-1}$ (based on liquid MeOH)
Reaction temperature: 320° C.
Mass ratio H$_2$S/MeOH: 1.9
Pressure: 9 bar The reaction mixture containing the products methylmercaptan, dimethyl sulfide and dimethyl ether and containing the unreacted starting materials methanol and hydrogen sulfide is analysed by online gas chromatography.

If halides are added to the catalyst, a marked increase in the activity is to be observed, with a simultaneous improvement in selectivity. Whereas in the prior art the selectivity falls in particular at high degrees of conversion, the same high selectivities are still noted even at very high conversions as a result of the addition of the halogens. This results in an increase in yield of up to 15% compared with the prior art. The selectivity can be increased to up to ~96.6% by adjusting the alkali tungstate-halide ratio. In the large-scale synthesis of methylmercaptan, this results in considerable cost savings in the separation of the reaction product from unreacted methanol and secondary products.

Furthermore, the results of the Examples show that the mutual replacement of at least some of the halides is possible in order to adjust the activity and selectivity of the catalyst in a targeted manner or in order to make savings in terms of raw material costs during catalyst production.

TABLE 1

Test results

| Catalyst Example | Molar ratio alkali:W | Halogen | Molar ratio halogen:alkali | Loading [wt. %] | Methanol conversion [%] | Selectivity [%] | Yield [%] |
|---|---|---|---|---|---|---|---|
| CE1 | 2:1 | — | 0 | 21.0 | 82.4 | 93.3 | 76.9 |
| CE2 | 2:1 | — | 0 | 26.3 | 79.5 | 94.7 | 75.2 |
| CE3 | 2:1 | — | 0 | 19.6 | 76.0 | 95.2 | 72.4 |
| E4 | 2:1 | F | 1:1 | 22.3 | 75.4 | 96.6 | 72.8 |
| E5 | 2:1 | Cl | 1:1 | 23.9 | 95.0 | 93.7 | 89.0 |
| E6 | 1.6:1 | Br | 0.2:1 | 18.5 | 92.4 | 94.5 | 87.3 |
| E7 | 2:1 | I | 1:1 | 29.6 | 88.9 | 95.5 | 84.9 |
| E8 | 2:1 | F, Br | 1:1 | 23.5 | 91.4 | 96.6 | 88.3 |

CE1: Catalyst according to Comparison Example 1

We claim:

1. Catalyst comprising a member selected from the group consisting of: (a) alkali tungstate, wherein the alkali tungstate contains a combination of two bonded alkali metals and selected from the group consisting of:
   a) potassium and caesium,
   b) sodium and caesium,
   c) rubidium and caesium,
   d) sodium and potassium,
   e) rubidium and potassium,
   and the alkali tungstate contains at least one halide selected from the group consisting of Cl, Br and I, wherein the molar ratio of the sum of the alkali metals to tungsten of from 0.9:1 to <4:1 and in a molar ratio of the sum of halides to the sum of alkali metals of from 0.01 : 1 to 3:1; and
   (b) alkali tungstate, wherein the alkali tungstate contains at least two halides selected from the group consisting of F, Cl, Br and I, with the proviso that the alkali metal is selected from at least one element of the group of the Periodic Table of Elements, wherein the tungstate contains at least one bonded alkali metal, tungsten and the at least two halides in a molar ratio of the sum of the alkali metals to tungsten of from 0.9:1 to <4:1 and in a molar ratio of the sum of halides to the sum of alkali metals of from 0.01 : 1 to 3:1.

2. Catalyst according to claim 1, wherein the tungstate in (b) contains a halide selected from the group consisting of F, Br and I.

3. Catalyst according to claim 1, wherein the molar ratio of alkali metal(s) to tungsten in the halide-containing alkali tungstate is from 2.2:1 to 0.9:1, and the molar ratio of halide (s) to alkali metal(s) is from 1:1 to 0.01:1.

4. Catalyst according to claim 1, further comprising a support material, wherein the support material is free of hydrohalic acid.

5. Catalyst according to claim 4, (a) which has the structure of a shell catalyst in which the core is a core surrounded by the alkali tungstate or (b) wherein the support material is impregnated with halide-containing alkali tungstate.

6. Catalyst according to claim 4, in which the support material impregnated with the halide-containing alkali tungstate is in the form of a uniform catalyst.

7. Catalyst according to claim 4, wherein the support material is shaped and has a surface impregnated with a catalytically active oxidic composition of alkali tungstate and halides with a molar ratio of alkali metal to tungsten of from 0.9:1 to <4:1 and a molar ratio of halide to alkali metal of from 0.01:1 to 3:1.

8. Catalyst according to claim 4, which comprises the halide-containing alkali tungstate in an amount of from 8 to 50 wt. %.

9. Catalyst according to claim 4, which comprises the halide-containing alkali tungstate in an amount of from 20 to 36 wt. %.

10. Catalyst according to claim 4, wherein the support body or the support material consists of an oxidic inorganic compound.

11. Catalyst according to claim 10, wherein the support body or the support material consists of aluminum oxide ($Al_2O_3$).

12. Catalyst according to claim 11, wherein the support material has a specific surface area of from 180 to 400 $m^2/g$ (BET) and a total pore volume of from 0.3 to 1.2 ml/g.

13. Catalyst according to claim 1, wherein the tungstate corresponds to the general formula (I) $A_xWO_yX_z$, wherein:
   for (a)
      A: represents two bonded alikali metals
      X: represents at least one halogen
      x: represents from 0.9 to <4
      y: represents oxygen content in the oxide
      z: represents from 0.01 to <12, and
   for (b)
      A: represents at least one alkali metal
      X: represents at least two halogens
      x: represents from 0.9 to <4
      y: represents oxygen content in the oxide
      z: represents from 0.01 to <12.

14. Catalyst according to claim 1, wherein the alkali tungstate contains an alkali metal selected from the group consisting of Na, K, Cs and Rb.

15. Process for the preparation of an alkylmercaptan comprising reacting an alkanol and hydrogen sulfide in the presence of the catalyst according to claim 1.

16. Process according to claim 15 for the preparation of methylmercaptan wherein the alkanol is methyl alcohol.

17. Catalyst comprising an alkali metal tungstate which contains at least one halide and a bonded alkali metal which is caesium and a hydrohalic acid-free support material.

18. Catalyst according to claim 17, wherein the tungstate contains a halide or two halides selected from the group consisting of F, Br, I and Cl.

19. Catalyst according to claim 17, wherein the tungstate contains caesium, tungsten and halide(s) in a molar ratio of caesium to tungsten of 0.9:1 to <4:1 and in a molar ratio of the sum of the halide(s) to caesium of 0.01:1 to 3:1.

20. Catalyst according to claim 19, wherein the molar ratio of caesium to tungsten is from 2.2:1 to 0.9:1, and the molar ratio of halide(s) to alkali metal is from 1:1 to 0.01:1.

21. Catalyst according to claim 17, wherein the catalyst is shell catalyst having a core that is coated with the tungstate or a support material impregnated with the tungstate.

22. Catalyst according to claim 21, wherein the support material impregnated with the tungstate is in the form of an extrudate.

23. Catalyst according to claim 17, wherein the support material is shaped and its surface is impregnated with caesium tungstate and halides with a molar ratio of caesium to tungsten of 0.9:1 to <4:1 and a molar ratio of halide(s) to caesium of 0.01:1 to 3:1.

24. Catalyst according to claim 17, wherein the tungstate corresponds to the general formula (I) $A_xWO_yX_z$, wherein:
A: represents caesium
X: represents at least one halide
x: represents from 0.9 to<4
y: represents oxygen content in the oxide
z: represents from 0.01 to <12.

25. Catalyst according to claim 17, wherein it contains the tungstate in an amount of 8 to 50% by weight.

26. Catalyst according to claim 17, wherein the support material consists of an oxidic inorganic compound.

27. Catalyst according to claim 26, wherein the support material consists of aluminum oxide ($Al_2O_3$).

28. Catalyst according to claim 27, wherein the support material has a specific surface area of 180 to 400 $m^2$/g (BET) and the total pore volume of 0.3 to 1.2 ml/g.

29. Process for preparing alkyl mercaptans by converting alkanols and hydrogen sulfide in the presence of the catalyst according to claim 26.

30. Process according to claim 29 for preparing methyl mercaptan by reacting methyl alcohol and hydrogen sulfide.

* * * * *